(12) United States Patent
Schick et al.

(10) Patent No.: US 7,551,720 B2
(45) Date of Patent: Jun. 23, 2009

(54) INSTALLATION OF A RECEIVER AS PART OF AN X-RAY TUBE HOUSING

(75) Inventors: David B. Schick, Flushing, NY (US);
Aaron Bratslavsky, Brooklyn, NY (US);
Stan Mandelkern, Teaneck, NJ (US);
Daniel Michaeli, Bronx, NY (US);
Michael C. Stone, Glen Cove, NY (US)

(73) Assignee: Schick Technologies, Long Island City, NY (US)

( * ) Notice: Subject to any disclaimer, the term of this patent is extended or adjusted under 35 U.S.C. 154(b) by 365 days.

(21) Appl. No.: 10/842,496

(22) Filed: May 11, 2004

(65) Prior Publication Data

US 2005/0254625 A1 Nov. 17, 2005

(51) Int. Cl.
*H05G 1/08* (2006.01)
*H05G 1/64* (2006.01)

(52) U.S. Cl. ............................. 378/91; 378/62; 378/98; 378/191

(58) Field of Classification Search ................ 378/98.8, 378/119, 121, 147, 189, 191, 196, 197, 198, 378/38, 62, 91, 98; 250/370.09
See application file for complete search history.

(56) References Cited

U.S. PATENT DOCUMENTS

| | | | | |
|---|---|---|---|---|
| 4,082,953 A * | 4/1978 | Krause et al. | ................. | 378/97 |
| 4,160,997 A | 7/1979 | Schwartz | ..................... | 358/93 |
| 4,166,220 A * | 8/1979 | Stutts | ........................ | 378/148 |
| 4,214,169 A * | 7/1980 | Hotta et al. | .................. | 378/147 |
| 4,259,583 A * | 3/1981 | Albert | ....................... | 378/98.6 |
| 4,893,321 A * | 1/1990 | Eitner et al. | ................ | 378/121 |
| 5,434,418 A * | 7/1995 | Schick | .................. | 250/370.11 |
| 5,631,943 A * | 5/1997 | Miles | ......................... | 378/102 |
| 5,693,948 A * | 12/1997 | Sayed et al. | ........... | 250/370.09 |
| 5,834,782 A | 11/1998 | Schick et al. | .......... | 250/370.11 |
| 5,852,647 A | 12/1998 | Schick et al. | ................ | 378/53 |
| 5,898,753 A | 4/1999 | Schick et al. | ................ | 378/54 |
| 5,908,294 A | 6/1999 | Schick et al. | ................ | 433/29 |
| 5,912,942 A | 6/1999 | Schick et al. | ............. | 378/98.8 |
| 5,995,583 A | 11/1999 | Schick et al. | ................ | 378/38 |
| 6,002,424 A | 12/1999 | Rapa et al. | ..................... | 348/66 |
| 6,038,287 A * | 3/2000 | Miles | ......................... | 378/117 |
| 6,069,935 A | 5/2000 | Schick et al. | ............. | 378/98.8 |
| 6,134,298 A | 10/2000 | Schick et al. | ............. | 378/98.8 |
| 6,320,934 B1 * | 11/2001 | Carroll et al. | ............. | 378/98.8 |
| 6,644,853 B1 * | 11/2003 | Kantor et al. | ............... | 378/203 |
| 6,697,453 B1 * | 2/2004 | Mueller et al. | ................ | 378/72 |
| 6,761,561 B2 | 7/2004 | Mandelkern et al. | ........ | 433/29 |
| D493,892 S | 8/2004 | Royzen et al. | ............ | D24/158 |
| 6,898,268 B2 * | 5/2005 | Makila et al. | ................ | 378/38 |
| 6,945,694 B2 * | 9/2005 | Kantor et al. | ............... | 378/203 |
| 6,950,496 B2 * | 9/2005 | Zimmermann et al. | ...... | 378/116 |
| 7,194,064 B2 * | 3/2007 | Razzano et al. | ............ | 378/98.8 |

(Continued)

*Primary Examiner*—Allen C. Ho
(74) *Attorney, Agent, or Firm*—Fitzpatrick, Cella, Harper & Scinto

(57) ABSTRACT

An x-ray system comprises an x-ray tube, covered by a housing, which emits x-rays therefrom, and a receiver mounted within the x-ray tube housing. An electronic sensor receives the emitted x-rays, converts the received x-rays into electrical image data signals, and transmits the electrical image data signals to the receiver. An image processing unit processes the electrical image data signals received from the receiver.

24 Claims, 4 Drawing Sheets

U.S. PATENT DOCUMENTS

| | | |
|---|---|---|
| 2002/0150214 A1 | 10/2002 | Spahn ........................ 378/189 |
| 2003/0152196 A1 | 8/2003 | Bratslavsky ................. 378/170 |
| 2003/0156681 A1* | 8/2003 | Cianciosi et al. .............. 378/38 |
| 2003/0228553 A1 | 12/2003 | Mandelkern ................. 433/29 |
| 2004/0065836 A1 | 4/2004 | Schick et al. .......... 250/370.01 |
| 2004/0065837 A1 | 4/2004 | Schick et al. .......... 250/370.08 |
| 2004/0066898 A1 | 4/2004 | Schick et al. .............. 378/98.9 |
| 2004/0152037 A1 | 8/2004 | Schick ........................ 433/29 |
| 2007/0223649 A1* | 9/2007 | De Godzinsky ................ 378/4 |

* cited by examiner

INSTALLATION OF A RECEIVER AS PART OF AN X-RAY TUBE HOUSING

BACKGROUND OF THE INVENTION

1. Field of the Invention

This invention relates generally to the field of x-ray systems, and more particularly to an x-ray receiver for medical and dental applications that is mountable within an x-ray tube housing.

2. Related Art

X-ray receptors have long been employed in the fields of medicine and dentistry to capture images representing the human anatomy. These images are often used by physicians and dentists to aid in the diagnosis and treatment of conditions and disease. In the case of dentists and oral surgeons, images of a patient's teeth, mouth, and gums are used to aid in diagnosis and treatment. The most conventional technique is to use radiographic film as the imaging receptor. However, solid-state sensors which convert x-rays into an electrical signal have increasingly begun to be used in place of photographic film.

Such filmless radiography systems offer many advantages over traditional film-based radiography. For example, an electronic sensor is typically more sensitive to x-rays than is film, thereby allowing the dosage of x-rays to the patient to be lowered quite significantly. Also, the image of the anatomy may be generated by the computer almost instantaneously, thus improving workflow and eliminating the entire film development process, including the use of potentially harmful chemicals. In addition, because the images are generated electronically, they can be easily stored in and accessed from a computer database.

In digital radiology, the signal from the electronic sensor is typically transmitted to a computer or other output device via a flexible cable. In other systems, however, a wireless interface may be substituted for the cable, such that signals are transmitted from the sensor to the output device via a radio-frequency waveform. Wireless communications systems have made inroads into many disciplines and may be preferable in medical and dental digital imaging for a number of reasons. For example, extra wires can be annoying to the patient and clinician. In addition, in certain diagnostic procedures, the sensor wires may be cumbersome and could limit placement of the sensor with respect to the x-ray tube and computer. In digital dental radiography, such wires can limit sensor placement in the mouth. Furthermore, mechanical failure of the wire due to strain is a common failure mechanism. A wire may also create a trip hazard.

In visible digital imaging, such as conventional digital photographic, the detector is typically integral to the camera housing, which might further include, among other things, a lens and image processing components, and in most cases a flash to augment the ambient light. Designing a camera in such a manner is relatively simple: ambient light and/or light provided by the flash reflects naturally off the subject and towards the detector housed in the camera.

In digital x-ray imaging, on the other hand, the energy source (e.g., the x-ray generator) is typically configured to provide the radiation directly towards the image detector, which is often distant from the source and/or from computer processing components. Thus, as discussed above, the image data is often conveyed from the detector using a long flexible cable, and in certain applications this cable can be inconvenient for the patient and the operator as it may present various electrical and mechanical constraints. A wireless system, on the other hand, can provide a wider range of degrees of freedom of the detector with respect to the source.

More particularly, in digital x-ray imaging, an x-ray beam is projected from an energy source towards an electronic sensor (in filmless dental radiography, for example, the electronic sensor is placed in the patient's mouth behind the tooth to be examined, and the x-ray beam is projected through the patient's tooth). The x-rays impinge on the electronic sensor, which converts the x-rays into an electrical signal. The electrical signal is typically transmitted over a wire to a computer as described above, and the computer then processes the signal to produce an image on an associated output device, such as a monitor or a printer. Alternatively, the electrical signal could be transmitted wirelessly from the electronic sensor to a receiver which in turn delivers the signal to the computer. The electronic sensor may include a charge-coupled device (CCD), an active pixel sensor (APS) array, or another type of filmless radiation sensor.

Examples of filmless radiography systems in the dental field include those described in U.S. Pat. No. 4,160,997 to Schwartz and U.S. Pat. No. 5,434,418 to Schick. An example of a wireless medical x-ray imaging system is provided by U.S. Patent Application Publication 2002/0150214 (Spahn). Spahn discusses a system in which a control unit communicates wirelessly with a detector. Spahn shows the receiver with which the detector communicates housed in a mobile central control device. While Spahn's design may offer some measure of flexibility, it suffers from a number of drawbacks in that it does not address certain technically challenging aspects of achieving its end. In practice, the distance from the transmitter to the receiver must typically be quite limited. This is because the waveform usually carries large volumes of data and may be blocked by obstructions such as medical equipment or the patient's anatomy. In yet other scenarios, such as in intra-oral dental imaging, there may be a limited amount of space available for the transmission circuitry within the sensor, and thus a less stable and lower power voltage controlled oscillator may be used. The overall power available to transmit a pulse may also be limited. And Federal regulatory bodies and hospitals commonly limit the amount of transmitted power that a design may utilize. Thus, the distance between the transmitter and receiver must typically be relatively short.

Moreover, it is often difficult to find a convenient and workable location for the receiver. Medical and dental offices typically contain furniture, equipment, and cabling that together limit the practical location for such a device. In dentistry, for example, an operating room might contain a dental chair, overhead lamps, instruments, trays and drills. Given factors such as these, finding an appropriate location for the receiver and its related circuitry is a formidable task.

Although prior art techniques are generally good for their intended purposes, they do not sufficiently address problems including those explained above. There exists, therefore, a need for finding a location for the receiver and its related circuitry which ameliorates the above-mentioned problems caused by, for example, practical factors such as the limited distance from the transmitter to the receiver, the limited space available for the transmission circuitry within the sensor, and the limited power requirements.

SUMMARY OF THE INVENTION

Accordingly, it is an object of this invention to provide an x-ray system which overcomes obstacles including those mentioned above. The invention is intended for use with wireless sensors or wired sensors.

It is also an object of this invention to provide a wireless x-ray receiver installation and setup which overcomes problems which have heretofore plagued the prior art.

It also is an object of this invention to provide a wireless receiver and its related circuitry in a location where problems caused by practical factors such as the limited distance from the transmitter to the receiver, the limited space available for the transmission circuitry within the wireless electronic sensor, and the limited power requirements, can be overcome. One advantage of the invention is that it allows medical and dental imaging detectors to more reliably transmit digital data to a computer or image processing unit.

It is also an object of this invention to provide an x-ray system for use with wireless or wired electronic sensors.

In accordance with the teachings of the present invention, these and other objects may be accomplished by the present invention, which in one embodiment is a wireless receiver conveniently mounted within a collimator or the housing of an x-ray tube for receiving x-ray imaging data to be transmitted to an image processing unit.

In another embodiment a wireless receiver comprises an antenna which may be slid into the cavity of the collimator or x-ray tube housing. The wireless receiver may be affixed to the inner diameter of the collimator or x-ray tube housing with adhesive, tape, or a clip. The receiver electronics may be housed inside the cavity or alternatively outside the housing in closer proximity to the image processing unit.

In another embodiment, a coil is provided in the collimator, and a wire transmits the information to a control box, where the x-ray tube settings are typically located. Interface electronics (such as those which utilize the Universal Serial Bus or USB of a computer) for the wireless sensor are located in the control box. The control box would preferably have a USB port through which the information could be passed directly to a computer.

Communication between the control box and the computer may be effected by way of a commonly available and accessible digital port such as, but not limited to, the USB. The USB is a serial 12 megabit per second (Mbps) channel that can be used for peripherals. The USB is a token-based bus; that is, the USB host controller broadcasts tokens on the bus and a device that detects a match on the address in the token responds by either accepting or sending data to the host. The host also manages USB bus power by supporting suspend/resume operations. The USB is advantageous in that it does not require the use of specially designed hardware inside the computer; once the appropriate software has been installed, a peripheral can be plugged into the USB port.

The computer's Peripheral Component Interconnect (PCI) bus and Industry Standard Architecture (ISA) bus also provide a data path between the electronic sensor and the computer's CPU. The PCI bus is an internal 32-bit local bus that runs at 33 MHz and carries data at up to 133 megabytes per second (Mbps), while the ISA bus is an 8- or 16-bit internal bus that carries data at up to 8.33 Mbps. Each of these buses may act as an interface between the sensor and the computer.

The invention in one embodiment provides an x-ray system, comprising an x-ray tube, covered by a housing, which emits x-rays therefrom, and a receiver mounted within the x-ray tube housing. An electronic sensor receives the emitted x-rays, converts the received x-rays into an electrical signal, and transmits the electrical signal to the receiver. An image processing unit is provided for processing the electrical signal received from the receiver. The receiver may include an antenna mounted inside the housing and circuitry mounted outside the housing. The receiver may be affixed to the inside of the x-ray tube housing one of an adhesive, tape, and a clip.

The invention in another embodiment provides an x-ray system, comprising an x-ray tube, covered by a housing, which emits x-rays. A receiver includes an antenna and circuitry, wherein the antenna is provided within the x-ray tube housing and the circuitry is provided outside the housing. An electronic sensor receives the emitted x-rays, converts the received x-rays into an electrical signal, and transmits the electrical signal to the receiver. An image processing unit processes the electrical signal received from the receiver.

The invention in another embodiment provides an x-ray system, comprising an x-ray tube, covered by a housing, which emits x-rays. A receiver includes an antenna and circuitry, wherein the antenna is provided within the x-ray tube housing and the circuitry is provided on an inside surface of the housing. An electronic sensor receives the emitted x-rays, converts the received x-rays into an electrical signal, and transmits the electrical signal to the receiver. An image processing unit processes the electrical signal received from the receiver.

The invention in another embodiment provides an x-ray system, comprising a collimator which collimates an x-ray beam and a receiver provided in the collimator. An electronic sensor receives the emitted x-rays, converts the received x-rays into an electrical signal, and transmits the electrical signal to the receiver. A control box receives the electric signal from the receiver, and an image processing unit processes the electrical signal received from the control box. The control box may communicate with the image processing unit through a wireless or wired interface, including, but not limited to, a Universal Serial Bus.

The invention in another embodiment provides an x-ray system, comprising means for emitting x-rays, and means for receiving the emitted x-rays, converting the received x-rays into an electrical signal, and transmitting the electrical signal. The system further comprises means provided within a housing of the emitting means for receiving the transmitted electric signal.

The invention in another embodiment provides a method for installing a wireless x-ray receiver for receiving an electrical signal from an electronic sensor, comprising the step of providing the receiver within an x-ray tube housing. The receiver may include an antenna mounted within the x-ray tube and circuitry mounted outside the tube.

The invention in another embodiment provides a receiver, comprising means for receiving electrical image data signals from an electronic sensor, and means for transmitting the electrical image data signals to an image processing unit, wherein the receiver is mounted within a housing of an x-ray tube which emits x-rays to the electronic sensor.

The invention in another embodiment provides a receiver, comprising means for receiving electrical image data signals from an electronic sensor, and means for transmitting the electrical image data signals to an image processing unit, wherein the receiver is mounted on an outside of a housing of an x-ray tube which emits x-rays to the electronic sensor.

The invention in another embodiment provides an x-ray system, comprising an x-ray tube, covered by a housing, and adapted to emit x-rays to an electronic sensor, and a receiver mounted on an outside of the x-ray tube housing, the receiver being adapted to receive electrical image data signals from the electronic sensor.

The invention in another embodiment provides an x-ray system, comprising an x-ray tube, covered by a housing, and adapted to emit x-rays, and a receiver located within the x-ray tube housing, adapted to receive electrical image data signals from a wireless sensor and produce a demodulated signal. An interface board located within the x-ray tube housing is adapted to receive electrical image data signals from a wired sensor and to receive the demodulated signal from the receiver, and produce an output signal that is compatible with an interface used for a uniform base station. The interface board may include a connector for receiving the electrical image data signals from the wired sensor. The x-ray system may further comprise an image processing unit, adapted to process the electrical image data signals received from the base station. The interface board may provide power to the wired sensor.

The invention in another embodiment provides an x-ray system, comprising an x-ray tube, covered by a housing, and adapted to emit x-rays, and a receiver located within the x-ray tube housing, adapted to receive electrical image data signals from a wireless sensor and produce a demodulated signal. An interface board located within the x-ray tube housing is adapted to receive electrical image data signals from a wired sensor and to receive the demodulated signal from the receiver, and to produce an output signal that is compatible with an interface used for a uniform base station. A control box is adapted to control the x-ray system and deliver the output signal to the base station.

BRIEF DESCRIPTION OF THE DRAWINGS

The invention will be more clearly understood by reference to the following detailed description of exemplary embodiments in conjunction with the accompanying drawings, in which.

DETAILED DESCRIPTION OF THE PREFERRED EMBODIMENTS

The invention will next be described in connection with certain exemplary embodiments; however, it should be clear to those skilled in the art that various modifications, additions, and subtractions can be made without departing from the spirit or scope of the claims.

The present invention is directed to x-ray systems, e.g., for use in medical or dental applications. The present invention may be used with charge-coupled devices (CCDs), active pixel sensor (APS) arrays, or any other suitable type of receptor.

As explained previously, one of the challenges related to wireless sensors has been to identify a practical and convenient location for the radiofrequency (RF) receiver and its related circuitry. The antenna should preferably be within reasonably close proximity to the transmitter that is typically housed within the sensor. On one hand, medical and dental offices typically contain furniture, equipment, and cabling that together limit the practical location for such a device. However, placing the receiver and its related circuitry at or near the interior of an x-ray tube or collimator (e.g., behind the electronics) ameliorates problems which have plagued the prior art.

In one embodiment of the invention, a wireless receiver comprises an antenna which is preferably slid into the cavity of an x-ray tube housing. The wireless receiver may be affixed to the inside surface of the x-ray tube housing with, e.g., adhesive, tape, or a clip. Of course, alternative embodiments are possible whereby the antenna is held into place by other suitable means, as would readily be envisioned by a person having ordinary skill in the art. The receiver electronics may be housed inside the cavity or alternatively outside the housing in closer proximity to the image processing unit. The receiver may be manufactured as part of an x-ray system, or may be provided as a separate device that can be mounted on the outside of an existing x-ray tube housing, for example (see FIG. 7). In this way, dental practitioners may benefit from the close proximity of the receiver mounted on an x-ray tube housing. Moreover, the antenna can be placed inside the x-ray tube housing in such a way as to allow easy replacement of the antenna or the x-ray tube. Alternatively, the antenna can be placed on the outside of the x-ray tube housing.

Figure 1:
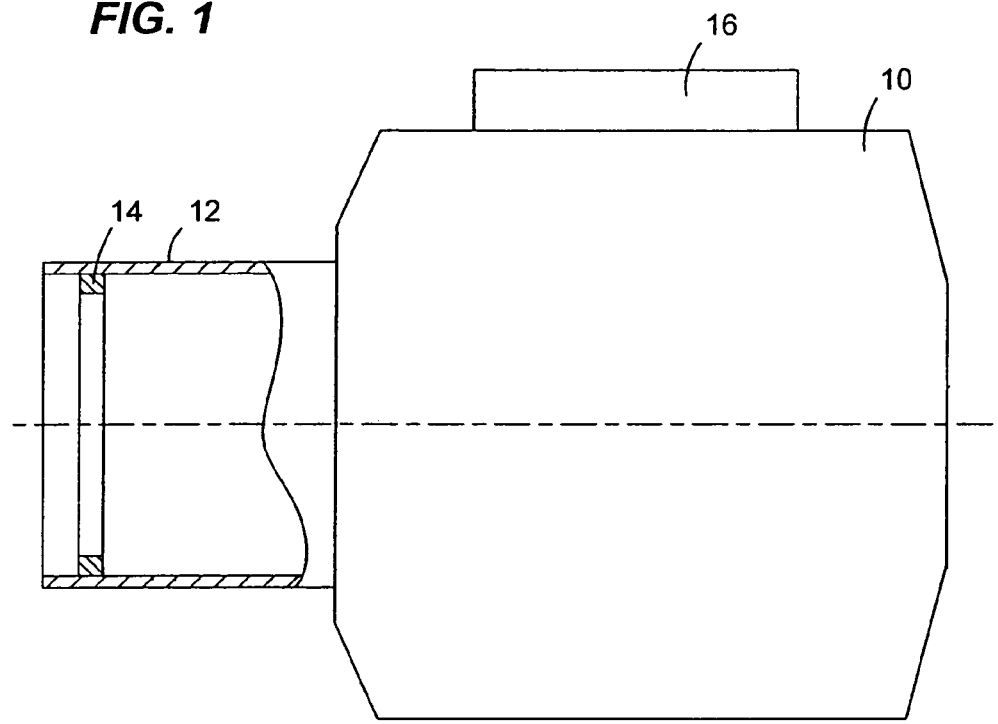
FIG. 1 is an illustration of one embodiment of the present invention using a wireless receiver.

A preferred embodiment of the present invention will now be described with reference to FIG. 1. FIG. 1 illustrates the placement of the antenna within the x-ray tube housing. The antenna is placed within the x-ray tube cone, collimator, or position-indicating device in a manner such that it is focused towards the detector and shielded from extraneous noise. The latter aspect is likely relatively trivial, since many of these locations would be inherently lead-lined. The antenna may be easily affixed using adhesive, tape, or a clip, as explained above, although other embodiments would be apparent to those skilled in the art. The receiver electronics may be housed inside the cavity or alternatively outside the housing in closer proximity to the image processing unit.

Figure 2:
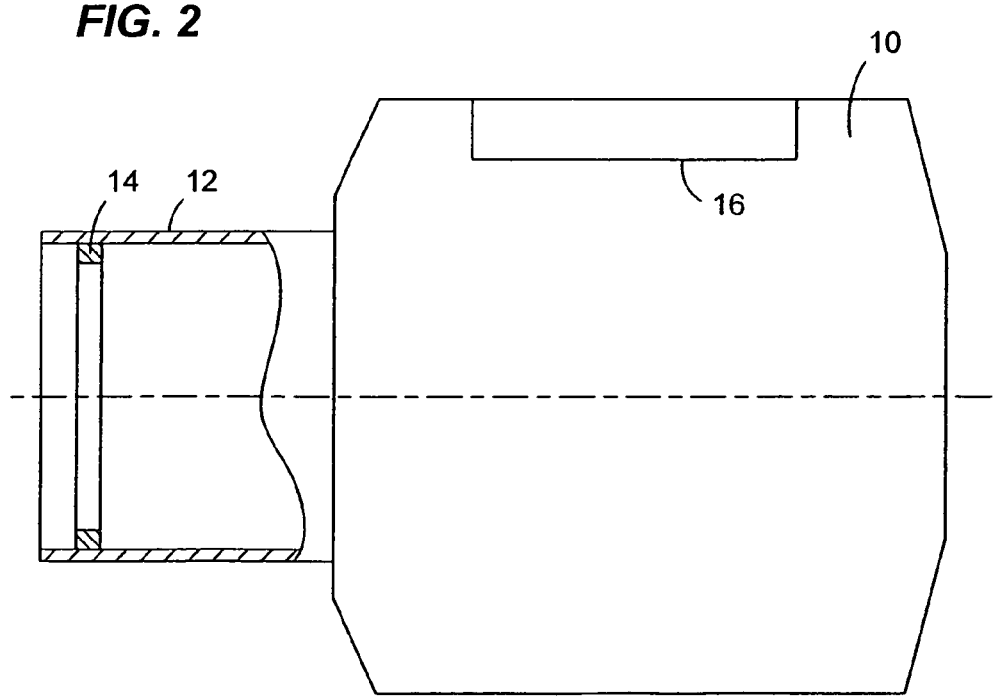
FIG. 2 is an illustration of another embodiment of the present invention using a wireless receiver.

Referring to FIG. 1, an x-ray tube housing 10 has a collimator 12 attached thereto. An antenna 14 is located inside the collimator 12 as seen in the figure in cross-sectional view. In this embodiment the receiver electronics 16 are located just outside the x-ray tube housing 10, although alternative locations are effective as well. For example, the receiver electronics 16 may be housed inside the cavity (as shown in FIG. 2 where like numerals correspond to similar components, although embodiments other than that shown in FIG. 2 are of course envisioned), or could be placed next to the computer. The receiver electronics 16 could also be manufactured and permanently located within the x-ray tube housing.

The x-ray tube emits x-rays to a wireless digital sensor (which for example, in the dental scenario, is located in a patient's mouth). The digital sensor converts the x-rays into an electrical signal and transmits the signal to the antenna 14 located inside the collimator 12 in the embodiment of FIG. 1. The information contained in the digital signal is then delivered to the image processing unit, which generates images for viewing and analysis and stores them in a database. The information may be delivered from the receiver to the computer through a second wireless interface, which would not be constrained by the size and power limitations that the sensor has. Alternatively, the information may be delivered from the receiver to the computer through a wired interface. In the latter case, a wire from the receiver would travel outside of the tube to the receiver electronics and a USB base station, for example.

In a wireless digital intra-oral dentistry system, the proposed antenna location is optimal since the x-ray source is typically within a linear foot of the detector and directed exactly towards the encapsulated antenna. The received signal may be conveyed to the receiver electronics and an image processing system or computer may be located near the x-ray tube.

In another embodiment, utilizing a wireless sensor, a coil is provided in the collimator, and a wire transmits the information to a control box where the x-ray tube settings are located. Typically, the control box is located at the end of an arm which the x-ray tube is attached to, the control box sometimes being mounted to a wall. In this embodiment, interface electronics (such as those which utilize the USB of a computer) for the wireless sensor are located in the control box. The control box would preferably have a USB port through which the information could be passed directly to a computer.

Therefore, in this embodiment, the signal is transmitted from the wireless sensor (which in the dental scenario is an intra-oral sensor located in the patient's mouth), is received by the receiver located in the collimator, and then a wire carries the information from the receiver to the control box, which is connected to the computer through, e.g., a USB port. The wire may feed through the arm to the control box.

It should be noted that various modifications and alterations may be made to this embodiment. For example, a wireless interface could be used to carry the information from the receiver to the control box instead of a wire. Or, in another example, the functionality of the control box and the computer could be combined in a single unit.

Figure 3:
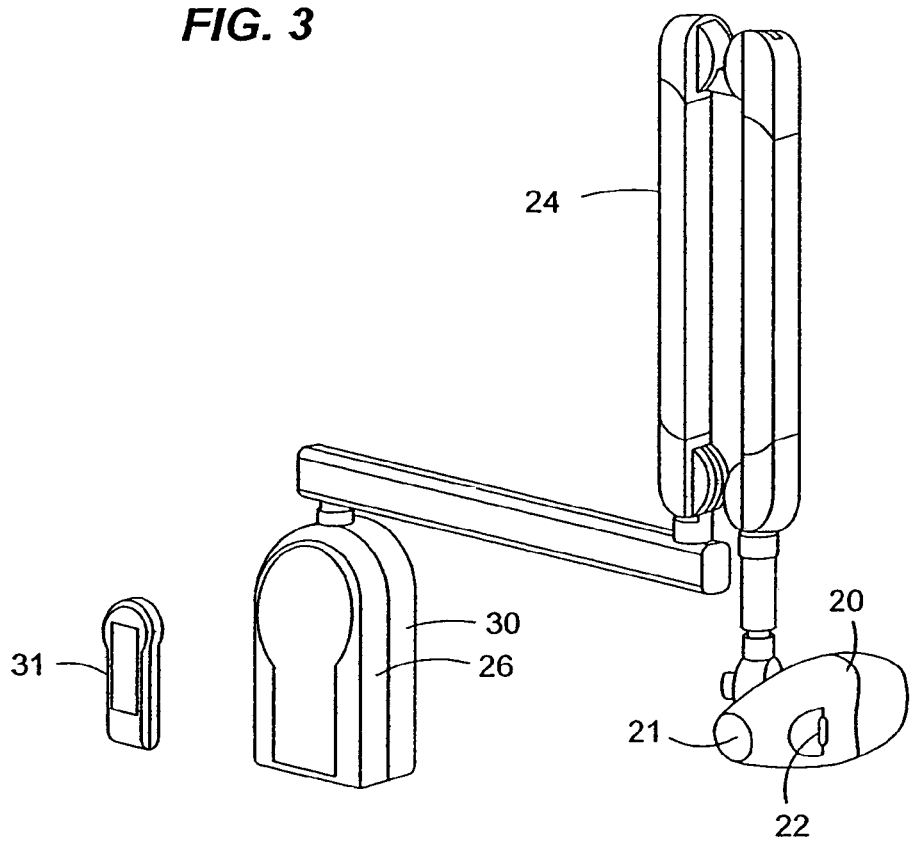
FIG. 3 is an illustration of an x-ray system for use with wireless or wired sensors according to a preferred embodiment of the present invention.

FIG. 3 is an illustration of an x-ray system for use with wired or wireless sensors according to a preferred embodiment of the invention. An antenna 21 located in the x-ray tube housing or enclosure 20 can receive data from a wireless sensor (not shown in the figure) situated, in the dental scenario for example, in a patient's mouth. Data is delivered to receiver circuitry and then to an interface board, both located in the x-ray tube housing, and a coaxial or other suitable cable delivers the image signal from the interface board through an extension arm assembly 24 to the wall mounted support 30. Data can also be received from a wired sensor via wired sensor interface 22, which is part of the interface board. A coaxial or other suitable cable delivers the image signal from the interface board through the extension arm assembly 24 to the wall mounted support 30. Timer box cover 26 is a modified front cover for the wall mounted support 30. The wall mounted support 30 and the timer box cover 26 are modified to include circuitry which carries out functions including acting as a timer box for controlling the x-ray system, for example via a hand-held or remote keypad 31. The timer box cover 26 and the wall mounted support 30 may be made from moldable plastic.

The x-ray system includes three modes of operation. First, the system can operate as a generic or standalone x-ray source. Second, the system can operate as a wireless x-ray source. Third, the system can operate as a wired x-ray source. In the second mode of operation, for example, the system can pick up the RF signal generated by a wireless sensor by way of antenna 21 inside the x-ray collimator. The signal is then routed through the wireless receiver circuitry for demodulation and through an interface board, and proceeds along the x-ray arm assembly 24 to the wall mounted support 30 enclosure. The output from the interface board, whether originally from a wired or wireless sensor, is made to be compatible with the interface used for a uniform base station. That is, this output, whether originally from a wired or wireless sensor, is made to have the same format when it is delivered through the arm to the timer box. The interface board is connected to a base station interface located outside the timer box in this embodiment.

Figure 4:
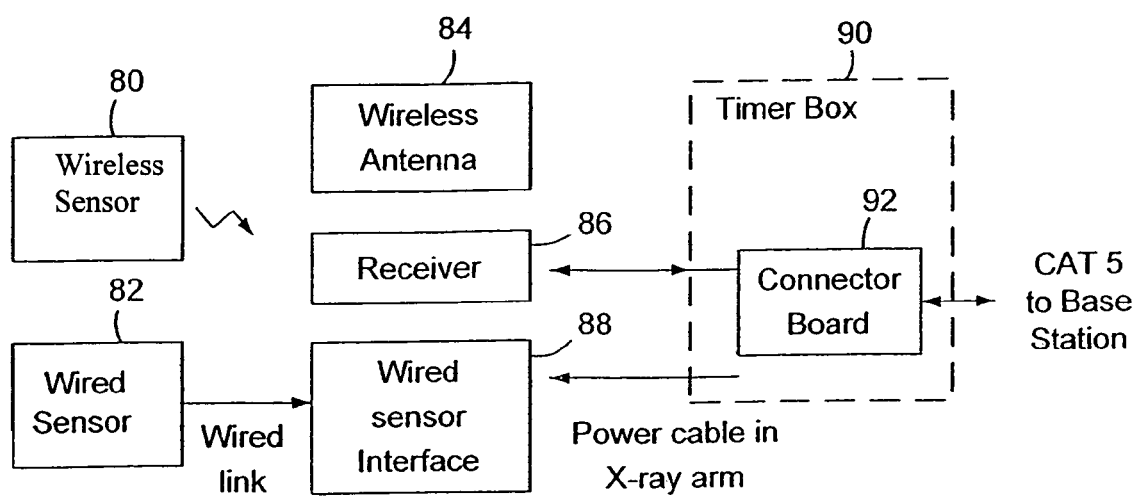
FIG. 4 is a block diagram of the x-ray system shown in FIG. 3.

FIG. 4 is a block diagram of the x-ray system shown in FIG. 3 according to a preferred embodiment of the invention. The system is designed to have the capability to receive data from a wireless sensor 80 or a wired sensor 82, and thus has both wireless and wired interfaces. In the case of a wireless sensor 80, antenna 84 in conjunction with receiver 86 operates to pick up the image signal transmitted from the wireless sensor 80, demodulate the signal, and deliver the processed signal through the interface board to a connector board 92 located in timer box 90. In the case of a wired sensor, data is delivered from the wired sensor 82 to wired sensor interface 88 which is part of the interface board and then to the connector board 92. The output from the interface board, no matter whether the signal originated from the wireless sensor 80 or the wired sensor 82, is made to be compatible with the interface used for the uniform base station.

Figure 5:
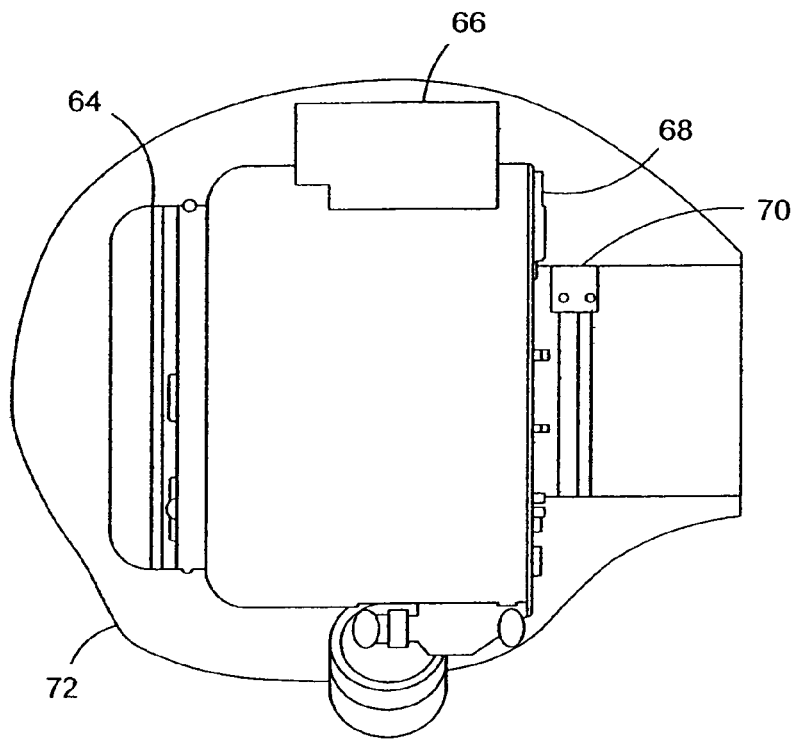
FIG. 5 is an illustration of another x-ray tube in accordance with the present invention.

FIG. 5 illustrates another x-ray tube in accordance with the present invention. The x-ray tube housing 72 includes receiver electronics 64, interface board 66, wired sensor connector 68, and antenna 70. For wireless sensors, antenna 70 receives an image signal from the sensor (not shown), and delivers the signal to receiver electronics 64 and then to the interface board 66. The signal is then sent, via either a wireless interface or a cable, to a control box and a uniform base station, and to an image processing unit which generates images for viewing and analysis. The receiver electronics 64 are directly connected to the interface board 66 to allow a single transfer point of data to the control (timer) box. The interface board 66 also serves as a connection point to the wired sensor as well as a mechanism for providing power and signals to the wired sensor.

For wired sensors, a cable carrying image information from the wired sensor plugs into the interface board 66 through the wired sensor connector 68. The interface board 66 is located, in this example, inside the x-ray tube housing 72 but other locations are envisioned, such as on the outside of the x-ray tube housing. The interface board 66 operates to process the signal from the sensor, performing such functions as driving the wired sensor, conditioning and formatting the signal into a more convenient format, and read-out of circuitry. The signal is then delivered, via either a wireless interface or a cable, through a control box and a base station to an image processing unit for viewing and analysis. With the setup described, the x-ray tube housing 72, which is in close proximity to the sensor, can act as an interface, and isolation of the signal can be achieved. The signal can be prevented from degrading as it is being passed along the arm to the control box. Of course, modifications to this embodiment are readily envisioned.

The system shown in FIGS. 3-5 uses a power source which may be part of a generic x-ray source. The receiver circuitry may derive power from a USB base station via, for example, a CAT 5 cable. USB version 1.1 is one example; of course, others could be used as well. A signal cable and a power cable may run through the x-ray arm assembly between the wired sensor interface and the connector board. The x-ray unit can be controlled via the hand-held keypad, with, for example, a coiled cable being used to connect the keypad to a CPU board in the wall mounted support 38, the coiled cable being fed through the enclosure via strain relief.

Figure 6:
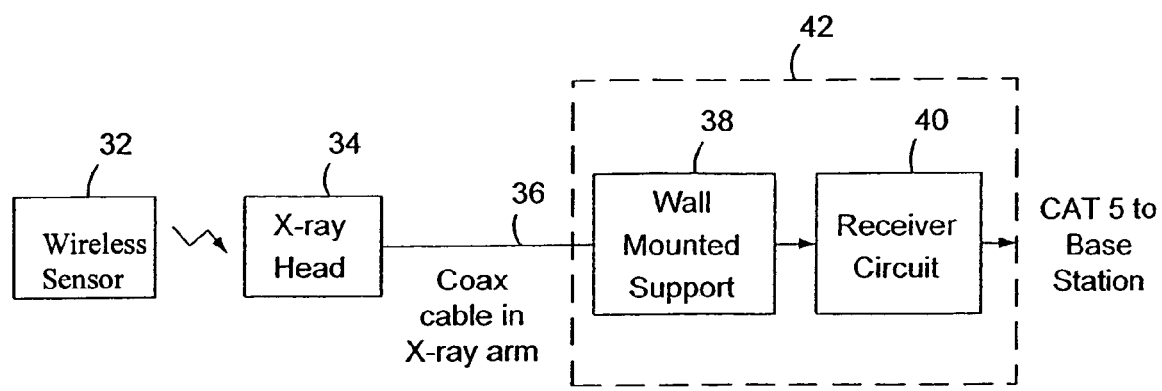
FIG. 6 is a block diagram of an x-ray system according to another embodiment of the present invention.

Various modifications on this design are envisioned. For example, in some embodiments the x-ray tube head might receive signals only from a wireless sensor and not from a wired sensor, or vice versa. Various components could be added or removed to suit a particular use. FIG. 6 is a block diagram of an embodiment using only a wireless sensor. In the figure, a wireless sensor 32 transmits data to an antenna (e.g., 2.4 GHz) located in x-ray housing or head 34. Cable 36, which is a coaxial or other suitable cable, runs from the antenna through an arm which the x-ray housing or head is attached to, and to the wall mounted support 38. Wireless receiver circuitry 40 is located in the timer box 42 and in this example may be connected to a computer through, e.g., a USB port.

Figure 7:
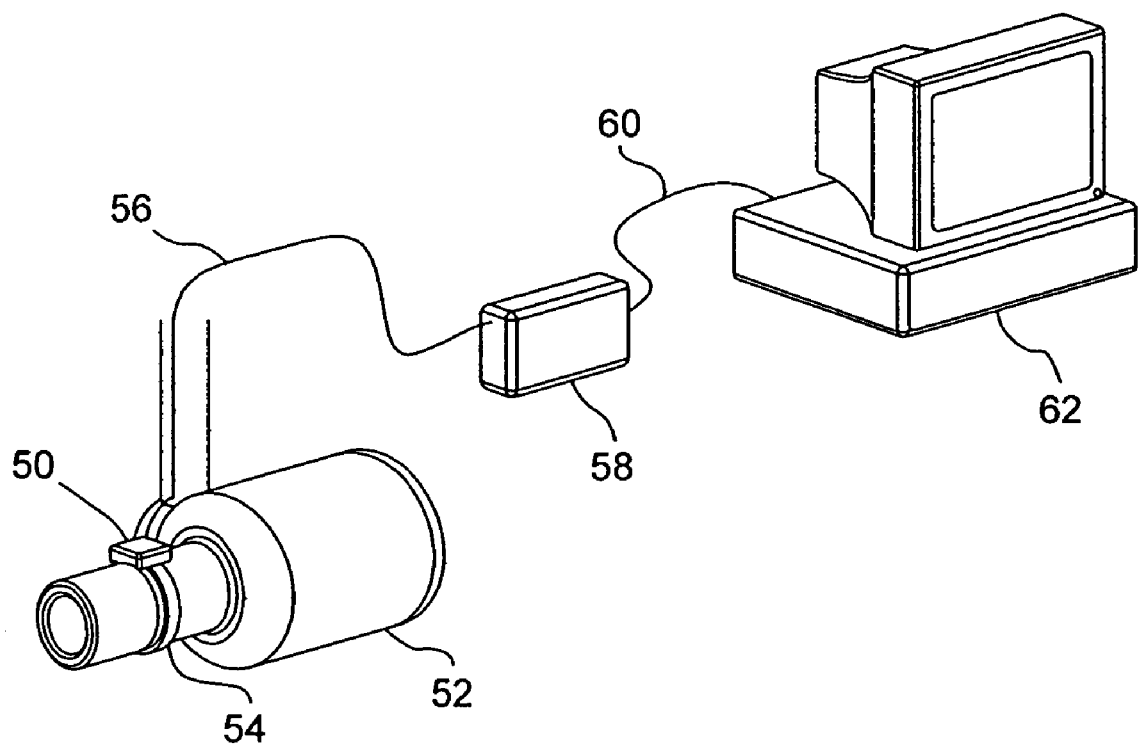
FIG. 7 is an illustration of another embodiment of the present invention.

FIG. 7 illustrates another embodiment in which a receiver 50 is mounted on the outside of an x-ray tube housing 52 by way of a receiver mount 54. Cable 56 carrying an electronic signal containing image information runs from the receiver 50 to the base station 58, which may be located on a stand of the x-ray tube, for example. The base station may put the information into, e.g., USB format. Cable 60 runs from the base station 58 to the image processing unit 62 which generates images for viewing and analysis and stores them in a database. Of course, in an alternative embodiment, the information may be delivered from the receiver to the image processing unit by way of a wireless interface.

While the invention has been particularly shown and described with respect to preferred embodiments thereof, it will be understood by those skilled in the art that changes in form and details may be made therein without departing from the scope and spirit of the invention.

Having described the invention, what is claimed as new and secured by Letters Patent is:

1. An x-ray system, comprising:
   an x-ray tube, covered by a housing;
   a collimator, which collimates an x-ray beam emitted from the x-ray tube;
   a receiver, having an antenna mounted within the collimator in a manner that shields the antenna from ambient radio frequency noise;
   an electronic sensor for receiving the emitted x-rays, converting the received x-rays into electrical image data signals, and wirelessly transmitting the electrical image data signals to the receiver; and
   an image processing unit for processing the electrical image data signals received from the receiver.

2. The x-ray system as set forth in claim 1, wherein the receiver further includes circuitry mounted outside the housing.

3. The x-ray system as set forth in claim 1, wherein the antenna is affixed to the inside of the collimator using one of an adhesive, tape, and a clip.

4. An x-ray system, comprising:
   an x-ray tube, covered by a housing, which emits x-rays;
   a collimator;
   a receiver including an antenna and receiver electronics, wherein the antenna is mounted within the collimator in a manner that shields the antenna from ambient radio frequency and the receiver electronics are provided on an outside surface of the housing;
   an electronic sensor for receiving the emitted x-rays, converting the received x-rays into electrical image data signals, and transmitting the electrical image data signals to the receiver; and
   an image processing unit for processing electrical image data signals received from the receiver.

5. The x-ray system as set forth in claim 4, wherein the antenna is affixed within the x-ray tube housing one of an adhesive, tape, and a clip.

6. An x-ray system, comprising:
   an x-ray tube, covered by a housing;
   a collimator, which collimates an x-ray beam emitted from the x-ray tube;
   a receiver including an antenna and circuitry, wherein the antenna is mounted within the collimator in a manner that shields the antenna from ambient radio frequency noise and the circuitry is provided on an inside surface of the housing;
   an electronic sensor for receiving the emitted x-rays, converting the received x-rays into electrical image data signals, and transmitting the electrical image data signals to the receiver; and
   an image processing unit for processing the electrical image data signals received from the receiver.

7. The x-ray system as set forth in claim 6, wherein the antenna is affixed within the collimator using one of an adhesive, tape, and a clip.

8. An x-ray system, comprising:
   a collimator which collimates an x-ray beam;
   a receiver, having an antenna mounted in the collimator in a manner that shields the antenna from ambient radio frequency noise;
   an electronic sensor for receiving emitted x-rays, converting the received x-rays into electrical image data signals, and transmitting the electrical image data signals to the receiver;
   a control box for receiving the electrical image data signals from the receiver; and
   an image processing unit for processing the electrical image data signals received from the control box.

9. The x-ray system as set forth in claim 8, wherein the receiver is affixed to the inside of the collimator using one of an adhesive, tape, and a clip.

10. The x-ray system as set forth in claim 8, wherein the control box communicates with the image processing unit through a wireless or wired interface.

11. The x-ray system as set forth in claim 10, wherein the wired interface is a Universal Serial Bus.

12. An x-ray system, comprising:
    means for emitting x-rays;
    means for collimating the emitted x-rays;
    means for receiving the collimated x-rays, converting the received x-rays into electrical image data signals, and wirelessly transmitting the electrical image data signals; and
    means for receiving the transmitted electrical image data signals, the receiving means being provided within the collimating means in a manner that shields the receiving means from ambient radio frequency noise.

13. An x-ray system, comprising:
    x-ray means for emitting x-rays;
    collimator means for collimating the x-rays emitted from the x-ray means;
    antenna means for wirelessly receiving electrical image data signals from an electronic sensor;
    transmitting means for transmitting the electrical image data signals to an image processing unit; and
    mounting means for mounting the antenna means within the collimator means in a manner that shields the antenna means from ambient radio frequency noise.

14. The x-ray system as set forth in claim 13, wherein the mounting means comprises one of adhesive, tape, and a clip.

15. An x-ray system, comprising:
    an x-ray tube, covered by a housing;
    a collimator, adapted to collimate an x-ray beam emitted from the x-ray tube;
    a receiver having an antenna located within the collimator in a manner that shields the antenna from ambient radio frequency noise, the receiver being adapted to receive electrical image data signals from a wireless sensor and produce a demodulated signal; and an interface board located within the x-ray tube housing, adapted to receive electrical image data signals from a wired sensor and to receive the demodulated signal from the receiver, and produce an output signal that is compatible with an interface used for a uniform base station.

16. The x-ray system as set forth in claim 15, wherein the interface board includes a connector for receiving the electrical image data signals from the wired sensor.

17. The x-ray system as set forth in claim 15, further comprising an image processing unit, adapted to process the electrical image data signals received from the base station.

18. The x-ray system as set forth in claim 15, wherein the interface board provides power to the wired sensor.

19. An x-ray system, comprising:

an x-ray tube, covered by a housing;

a collimator, which collimates an x-ray beam emitted from the x-ray tube;

a receiver having an antenna located within the collimator in a manner that shields the antenna from ambient radio frequency noise, the receiver being adapted to receive electrical image data signals from a wireless sensor and produce a demodulated signal; and an interface board located within the x-ray tube housing, adapted to receive electrical image data signals from a wired sensor and to receive the demodulated signal from the receiver, and to produce an output signal that is compatible with an interface used for a uniform base station;

a control box, adapted to control the x-ray system and deliver the output signal to the base station.

20. The x-ray system as set forth in claim 19, further comprising an image processing unit, adapted to process data received from the base station.

21. The x-ray system as set forth in claim 19, wherein the interface board includes a connector for receiving the electrical image data signals from the wired sensor.

22. A method for installing a wireless receiver for receiving an electrical signal from an electronic sensor which converts x-rays into an electrical image data signal, comprising the step of providing an antenna of the receiver within a collimator of an x-ray tube housing in a manner that shields the antenna from ambient radio frequency noise.

23. The method as set forth in claim 22, further comprising the step of affixing the antenna within the collimator using one of an adhesive, tape, and a clip.

24. The method as set forth in claim 22, wherein the receiver further includes circuitry mounted on an outside surface of the x-ray tube housing.

* * * * *